(12) United States Patent
Duenas Sanchez

(10) Patent No.: US 7,024,761 B2
(45) Date of Patent: Apr. 11, 2006

(54) DEVICE FOR DESTROYING SHARP, POINTED OBJECTS WHICH IS FITTED WITH MEANS FOR AUTOMATICALLY UNSCREWING INJECTING NEEDLES AND SIMILAR

(75) Inventor: Silverio Duenas Sanchez, Granada (ES)

(73) Assignee: Saraito, S.L., Granada (ES)

( * ) Notice: Subject to any disclaimer, the term of this patent is extended or adjusted under 35 U.S.C. 154(b) by 0 days.

(21) Appl. No.: 10/487,310

(22) PCT Filed: Aug. 28, 2001

(86) PCT No.: PCT/ES01/00332

§ 371 (c)(1),
(2), (4) Date: Feb. 20, 2004

(87) PCT Pub. No.: WO03/018090

PCT Pub. Date: Mar. 6, 2003

(65) Prior Publication Data
US 2004/0231149 A1    Nov. 25, 2004

(51) Int. Cl.
*B23P 19/00* (2006.01)
(52) U.S. Cl. .................... 29/801; 29/777; 29/401.1; 29/426.4; 29/426.5
(58) Field of Classification Search .............. 29/801, 29/401.1, 426.4, 426.5, 777; 219/68; 83/944; 128/919; 604/110; 206/366
See application file for complete search history.

(56) References Cited

U.S. PATENT DOCUMENTS

| 4,417,460 A | * | 11/1983 | Moriconi ................ 72/325 |
| 4,531,437 A | * | 7/1985 | Szablak et al. .......... 83/165 |
| 5,076,178 A | * | 12/1991 | Kohl et al. .............. 110/250 |
| 5,091,621 A | * | 2/1992 | Butler ................... 219/68 |
| 5,138,124 A | * | 8/1992 | Kirk et al. .............. 219/68 |
| 5,138,125 A |   | 8/1992 | Salesses |
| 5,166,488 A | * | 11/1992 | Peppard ................ 219/759 |
| 5,168,612 A | * | 12/1992 | Schultz et al. ........ 29/33 R |
| 5,188,598 A | * | 2/1993 | Thead et al. ........... 604/110 |
| 5,268,549 A | * | 12/1993 | Butler ................... 219/68 |
| 5,277,868 A | * | 1/1994 | Langford .............. 422/21 |
| 5,282,428 A | * | 2/1994 | Greville et al. ........ 110/250 |
| 5,287,609 A | * | 2/1994 | Chang .................. 29/33 R |

(Continued)

FOREIGN PATENT DOCUMENTS

EP    0 913 163    5/1999

(Continued)

*Primary Examiner*—Essama Omgba
(74) *Attorney, Agent, or Firm*—Jordan and Hamburg LLP

(57) ABSTRACT

A sharp cutting object disposal device provided with means for automatic unscrewing of venopuncture needles and the like, consisting of a tube to which a pair of motors or a gear wheel are fixed, the wheel which, actuated by a geared part that upon sliding on the gear wheel, will cause the rotation of the latter and in turn, this gear wheel will move several gears which will make two cylindrical and solid contacts turn, carrying out the disposal of the needle by means of friction plus the passing of electric current, provided with a conduit inside for exhaust of gases produced by melting the needle, without needing ventilators or any other forced air system, in addition to having another tube for separating the needle from the "screw-on" type syringe during the same needle disposal operation, the inside of the drawer having a housing recipient for the needle wastes, and another recipient incorporated inside the container for housing the plastic needleless syringes or non-sharp hospital wastes, and inside this container, there is an ozone or ultraviolet valve for sterilizing the needles.

6 Claims, 15 Drawing Sheets

U.S. PATENT DOCUMENTS

| | | | |
|---|---|---|---|
| 5,312,346 A | | 5/1994 | Han |
| 5,336,862 A | * | 8/1994 | Yelvington ................... 219/68 |
| 5,351,381 A | * | 10/1994 | Case .......................... 29/283.5 |
| 5,391,849 A | * | 2/1995 | Furuya et al. ................ 219/68 |
| 5,468,928 A | * | 11/1995 | Yelvington ................... 219/68 |
| 5,540,416 A | * | 7/1996 | Huang ........................ 266/200 |
| 5,545,869 A | * | 8/1996 | Piva .......................... 219/68 |
| 5,548,095 A | * | 8/1996 | Cornell ....................... 219/68 |
| 5,551,355 A | * | 9/1996 | Haines et al. ............... 110/242 |
| 5,573,113 A | | 11/1996 | Shillington et al. |
| 5,676,859 A | | 10/1997 | Yanobu |
| 5,741,230 A | * | 4/1998 | Miller ........................ 604/110 |
| 5,852,267 A | | 12/1998 | Yanobu |
| 5,868,709 A | * | 2/1999 | Champion et al. ........... 604/110 |
| 5,874,054 A | * | 2/1999 | Yelvington .................. 422/309 |
| 5,877,469 A | * | 3/1999 | Truesdale et al. ............. 219/68 |
| 6,051,802 A | * | 4/2000 | Davis et al. ................... 219/68 |
| 6,148,742 A | * | 11/2000 | Constable et al. .......... 110/250 |
| 6,169,259 B1 | * | 1/2001 | Hall et al. ..................... 219/68 |
| 6,169,260 B1 | * | 1/2001 | Akutsu et al. ................. 219/68 |
| 6,712,207 B1 | * | 3/2004 | Panek et al. ................. 206/366 |
| 6,745,898 B1 | * | 6/2004 | Lin ............................. 206/366 |
| 6,792,662 B1 | * | 9/2004 | Samuel ..................... 29/426.5 |
| 2002/0074315 A1 | * | 6/2002 | Decaire et al. ............. 219/69.1 |
| 2005/0121343 A1 | * | 6/2005 | Miller et al. ................ 206/366 |

FOREIGN PATENT DOCUMENTS

| | | | |
|---|---|---|---|
| EP | 0 947 210 | | 10/1999 |
| JP | 05253300 A | * | 10/1993 |
| WO | WO-9638255 | | 12/1996 |

* cited by examiner

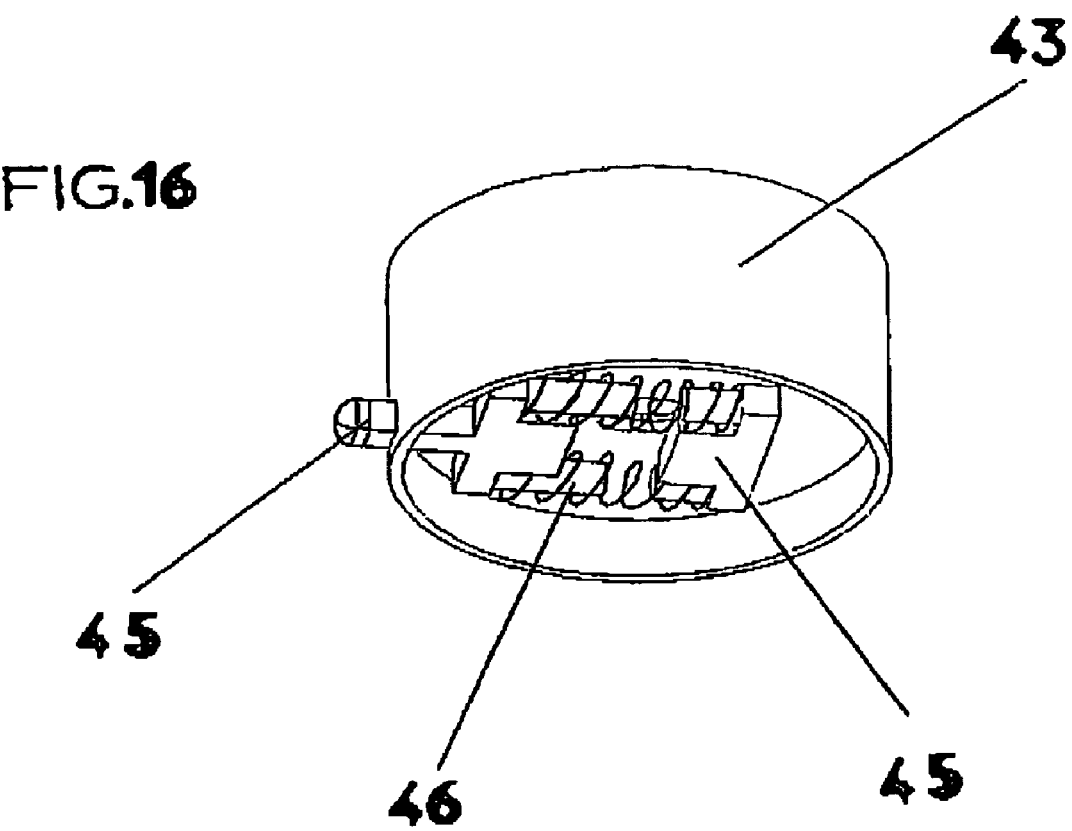
FIG.16
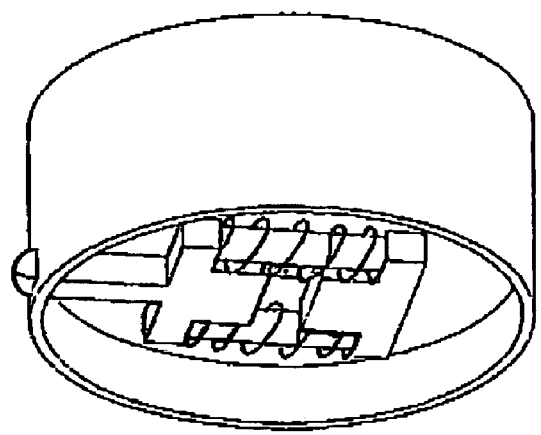

DEVICE FOR DESTROYING SHARP, POINTED OBJECTS WHICH IS FITTED WITH MEANS FOR AUTOMATICALLY UNSCREWING INJECTING NEEDLES AND SIMILAR

BACKGROUND OF THE INVENTION

The present specification refers to a Patent of Invention application regarding a sharp cutting object disposal device provided with means for automatic unscrewing of venopuncture needles and the like, whose evident purpose is based on being configured as a device fed by electric power, capable of massively disposing of sharp cutting object such as hypodermic needles, scalpel blades and other objects constituting single use surgical instruments, practically instantaneously.

The invention acts with the collaboration of one or two motors fed by electric current, powered with the electric current passing through their rotating contacts, or through a gear wheel which rotates when a part which is also geared moves over the former, on whose upper part a cylinder is fixed moving up or down due to the pressure of a syringe with its needle.

The invention is provided with a device intended for exhausting the gases produced inside due to the disposal of the needles through a conduit or chute, which has an activated carbon filter inside intended for retaining the heated particles going up.

Likewise, the invention has means for automatic unscrewing of the needles connected to the syringes which acts as the venopuncture, hypodermic needles or the like are being disposed of.

A plastic container adhered to the machine has also been placed, inside of which there is an ozone or ultraviolet valve for sterilizing the objects which are not sharp cutting, such as syringes or cotton, in addition to using replaceable cardboard containers or plastic bags inside this plastic container.

The applicant has knowledge of the existence of a plurality of drawbacks derived from involuntary punctures in medical and surgical centers where needles are used; drawbacks which obviously are not precisely corrected with the use of protective material as well as with plastic containers to later be transported and incinerated.

The applicant knows of the existence of recipients of a rigid material provided with an inlet inside of which sharp cutting objects are gradually deposited as they are disposed of, then specialized staff remove these recipients containing the wastes which are subsequently taken to facilities where they are massively disposed of, either by melting, or by autoclave, etc.

It has been shown that, as these are blind recipients, in other words, provided with inlets through which the disposable material manufactured of metal is introduced, occasionally, the incorporated objects are placed inside in strange positions, remaining next to the inlet, which leads to causing cuts or lesions upon carrying out a new removal of these elements.

The applicant has knowledge of the existence of the European Patent of Invention EP-0 947 210 regarding an "APARATO PARA LA DESTRUCCIÓN DE AGUJAS HIPODÉRMICAS Y DE ADENOPUNCIÓN" (NEEDLE DISPOSAL APPARATUS).

The applicant likewise knows the existence of the U.S. Pat. No. 5,676,859 regarding an "APARATO PARA LA DESTRUCCIÓN DE AGUJAS HIPODÉRMICAS Y SIMILARES" (INJECTION NEEDLE SAFETY DISPOSAL APPARATUS).

By the U.S. Pat. No. 5,138,124, an "APARATO PARA LA DESTRUCCIÓN DE AGUJAS HIPODÉRMICAS" (APPARATUS FOR THE DISPOSAL OF HYPODERMIC NEEDLES) is known.

By the PCT Patent No. WO 96/38255, an "APARATO PORTÁTIL PARA DESTRUIR AGUJAS" (PORTABLE APPARATUS FOR DISPOSING OF NEEDLES) is known.

By the U.S. Pat. No. 5,852,267, an "APARATO PARA ELIMINAR AGUJAS DE INYECCIONES" (INJECTION NEEDLE SAFETY DISPOSAL APPARATUS) is known.

By the U.S. Pat. No. 5,138,125, an "APARATO ALIMENTADO POR ENERGÍA ELÉCTRICA PARA LA DESTRUCCIÓN Y ESTERILIZACIÓN DE AGUJAS" (ELECTRIC NEEDLE DISPOSAL DEVICE WITH STERILIZABLE ASSEMBLY) is known.

By the U.S. Pat. No. 5,188,598, an "APARATO Y MÉTODO PARA LA DESTRUCCIÓN DE AGUJAS EVITANDO LA CONTAMINACIÓN" (APPARATUS AND METHOD FOR SAFELY DISPOSING CONTAMINATED NEEDLES) is known.

By the European Patent No. EP-913 163, an "APARATO PARA LA DESTRUCCIÓN DE AGUJAS HIPODÉRMICAS POR MEDIOS ELECTROMAGNÉTICOS" (NEEDLE DISPOSAL APPARATUS WITH REDUCED ODORS, ENHANCED SAFETY AND REDUCED ELECTROMAGNETIC NOISE) is known.

However, the applicant has no knowledge of the current existence of an invention capable of disposing of the needle at the same time that as the unscrewing thereof from the adaptation area on the syringe or the like, likewise having no knowledge of the existence of an invention having a plastic deposit placed against the invention or the inside thereof, inside of which deposit replaceable cardboard containers or plastic bags with a certain thickness can be placed, where the objects which are not sharp or cutting are placed to later be sterilized by means of an ozone or ultraviolet valve, which leads to significantly reducing the cost of rigid plastic containers, since, upon disposing of the sharp object, the syringes can be placed in a cardboard container or plastic bag since the sharp object was already disposed of.

BRIEF SUMMARY OF THE INVENTION

The sharp cutting object disposal device provided with means for automatic unscrewing of venopuncture needles and syringe sterilization system proposed by the invention is itself configured as an evident novelty within its field of application, because, apart from the features shown to be suitable for its actuation, it permits automatically unscrewing the needle from the syringe without there being any need to carry out this operation manually by manually capping the needle with the cap to unscrew it and remove it, and thus preventing an accidental puncture, and at the same time disposing of the needle as it is unscrewed in order for the latter to be deposited in a specific container, the syringe housing container being incorporated or inside of the machine for its subsequent sterilization.

More specifically, the sharp cutting object disposal device provided with means for automatic unscrewing of venopuncture needles or the like object of the invention, is constituted as an apparatus fed by electric power from the electric network as well as from a battery, to which a container is adjacently incorporated for the wastes of the objects which are not sharp, such as the syringes, sterilized by means of an ozone or ultraviolet valve, and a second recipient or container for the disposed wastes of sharp cutting objects, also having a gas exhaust system or conduit lacking a ventilator or system forcing the gases out which are produced inside due to the disposal of the needle, in whose upper part a filter with the suitable specifications will be installed.

The disposal of the sharp cutting objects is carried out by introducing the object to be disposed of through an opening incorporated on a tubular structure, in which a pair of motors or a gear wheel are fixed, actuated by a saw-toothed part which, upon sliding on the gear wheel, will cause the latter to rotate, and in turn, this gear wheel will move several gears which will make two cylindrical and solid contacts turn.

These aforementioned contacts are fed with electric current through brushes located inside of brush holders and in turn through the pertinent electric wires or conductors.

The invention is capable of carrying out the disposal of the sharp cutting objects by means of the actuation of a single motor, which generates movement in one of the shafts on which a solid contact is assembled, in this manner, one of the contacts is fixed and the other is movable, actuated by the motor's rotation.

These shafts have two solid contacts at the end thereof which rotate and which receive current from the brushes, by means of the electric current passage plus the friction due to the rotation, they carry out the disposal of the needles or of the scalpel blades.

Inside, the device has a tube or chimney located in the upper part of the solid contacts for the purpose of permitting the exhaust of gases produced by the melting required for disposing of the needles, lacking a ventilator or system forcing the gas exhaust, the gases being retained in the upper part of the tube by means of an activated carbon filter which prevents harmful particles from passing through which, due to the effect of the heat produced by melting the needle, go up this tube where a hollow, screw-on cap is placed on the end thereof.

Another tube is placed at a 45° angle to the tube vertical, serving as a conduit for the needles to the solid contacts where they are disposed of, likewise having means for unscrewing the needles from the so-called "screw-on" type syringes.

Said tube has a helical shaped track or rail inside which begins and ends on both sides or on one side, depending on the rotation carried out by the cylindrical part inside of the tube, there being on the inside thereof a cylindrical part with vertical and rotational movement originating from the existence of said track or rail, cylindrical part in turn provided with two Y-shaped metallic parts, which slide horizontally inside the cylindrical part and due to the action of two springs, these preventing said parts from joining together, unless they are pressed on their ends in the form of lugs.

As the aforementioned cylindrical part vertically slides downwards through the tube, a movement carried out due to the pressure created by a syringe, turning the needle as it goes down in a counter-clockwise or clockwise direction, according to where the direction of the track or rail is inclined, and keeping the syringe in place, the needle moving from the upper part of the tube down to the lower part, pressing on a spring in its path and during this vertical, downward path of the cylindrical part, said "Y"-shaped parts will be joined at their ends opposite the lugs and upon reaching the lower part of the tube, the lugs will project through the openings or holes provided for that purpose due to the force originated from springs, being necessary to point out that that once the pressure of the syringe against the cylindrical part has ended and the needle has consequently been unscrewed from the syringe, the downward force of a spring will make the cylindrical part go up again to its upper or standstill position, again permitting carrying out a similar one for unscrewing the needles.

The cylindrical part can also be prevented from turning when the part is going down through the tube, as this other tube has a system of one or two straight and hollow parallel rails on only one side of the tube or in both sides thereof in which the lug or lugs of the cylindrical part will be maximally separated from its ends opposite the lugs; thus, the cylindrical part will carry out an upward or downward movement without carrying out any type of rotation for those needles which are not of the "screw-on" system, and for those needles which are, inside the tube, a system of inner inclined rails or tracks will be provided, as previously indicated.

In this entire downward process, the cylindrical part unscrews the needle, which is also disposed of, since it is provided for that the rotating solid contacts are in the lower part of the tube.

Likewise, once the sharp cutting objects have been disposed of by the previously disclosed mechanisms, the non-sharp or non-cutting objects, such as the syringe, are going to be sterilized with an ozone or ultraviolet valve, this valve fed by a battery or electrical transformer; this valve is arranged in the adjacent container for collecting this type of material, and once this material has been exposed to the different valves, it will be completely sterilized.

BRIEF DESCRIPTION OF THE DRAWINGS

To complement the description being made and for the purpose of helping to better understand the features of the invention, a set of drawings is attached to the present specification as an integral part thereof, which, with an illustrative and non-limiting character, show the following:

FIG. 16. shows a perspective view of the cylindrical part with a movable lug and another fixed one on the inside thereof, in standstill and working position;

DETAILED DESCRIPTION OF THE INVENTION

Figure 7:
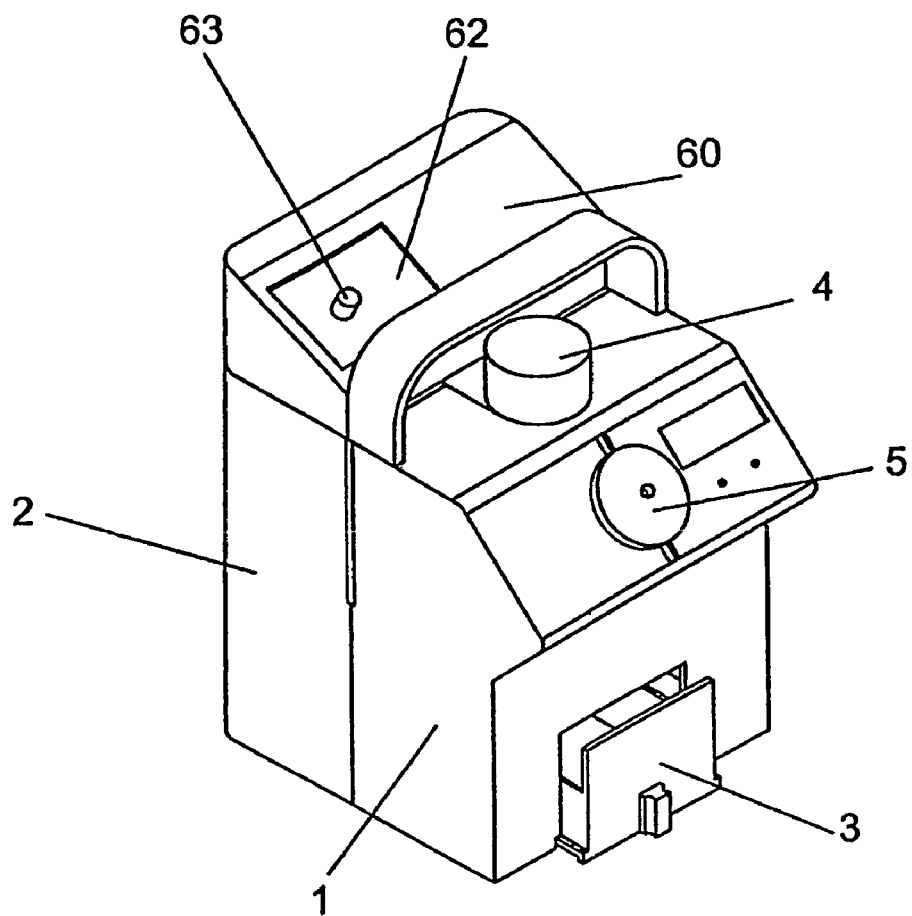
FIG. 7. shows a perspective view of the object of the invention from the upper area.

Following FIG. 7, it can be seen how the sharp cutting object disposal device provided with means for automatic unscrewing of venopuncture needles and the like, configured as a general body referenced with 1, showing a container for needleless syringes 2 in the rear part, and a drawer with a container neither shown nor referenced in the lower part referenced with 3, incorporated in the recipient deposit for needleless syringes, there is an additional and auxiliary recipient 70, preferably made of cardboard or tetra-pack, or from plastic bags provided with a suitable thickness, according to its application.

The invention is provided with an activated carbon filter 4 and an opening 5 intended for being used for introducing the sharp cutting objects.

Figure 11:
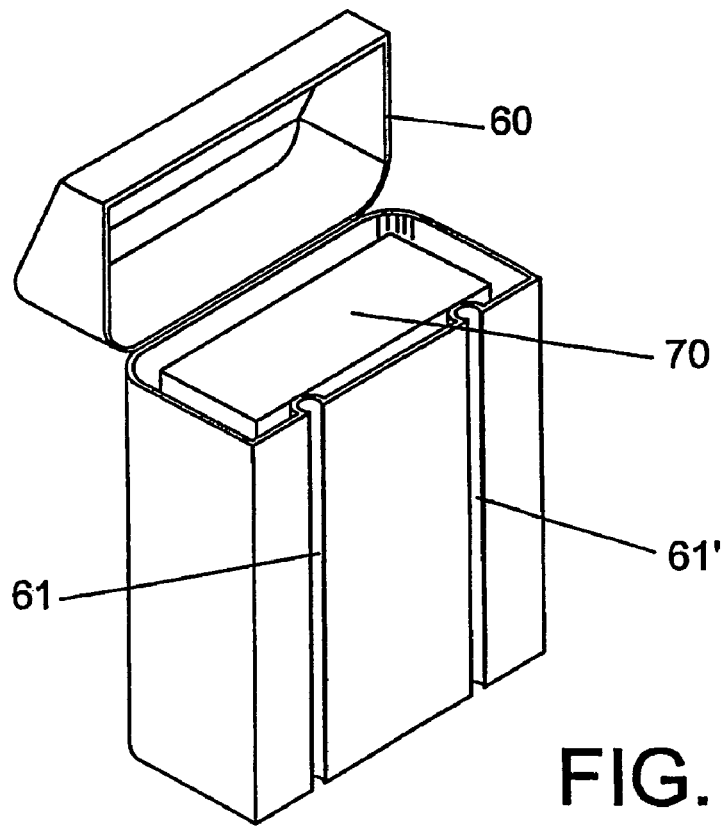
FIG. 11. shows a view of the object shown in FIG. 10, in which the inside access cover is open, where it is possible to see the cardboard container housing the syringes, which will be removed and replaced by another when full.
Figure 12:
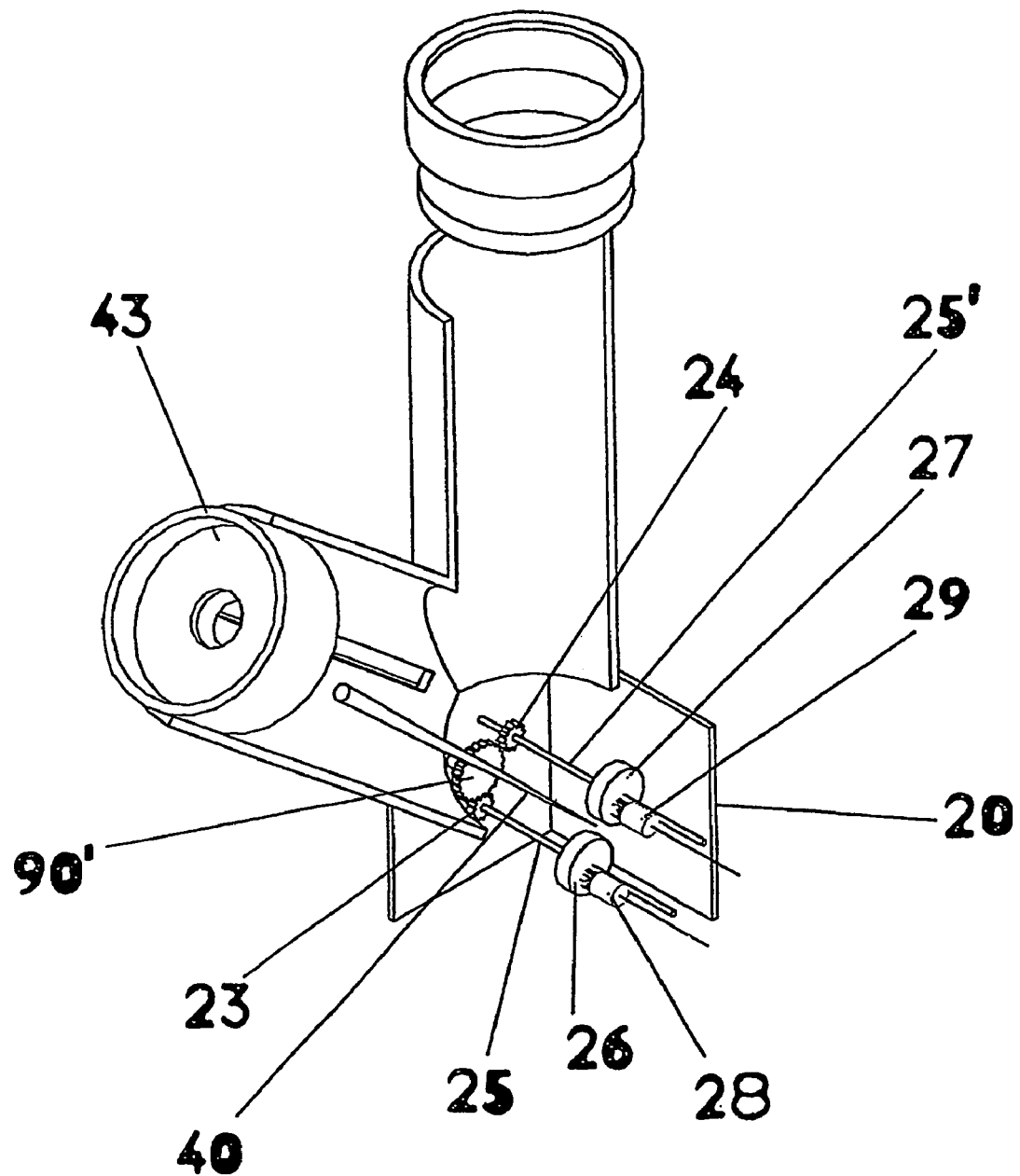
FIG. 12. shows the tube of FIG. 1 but from the inside part thereof, where the gears and solid contacts disposing of the needle can be seen.
Figure 13:
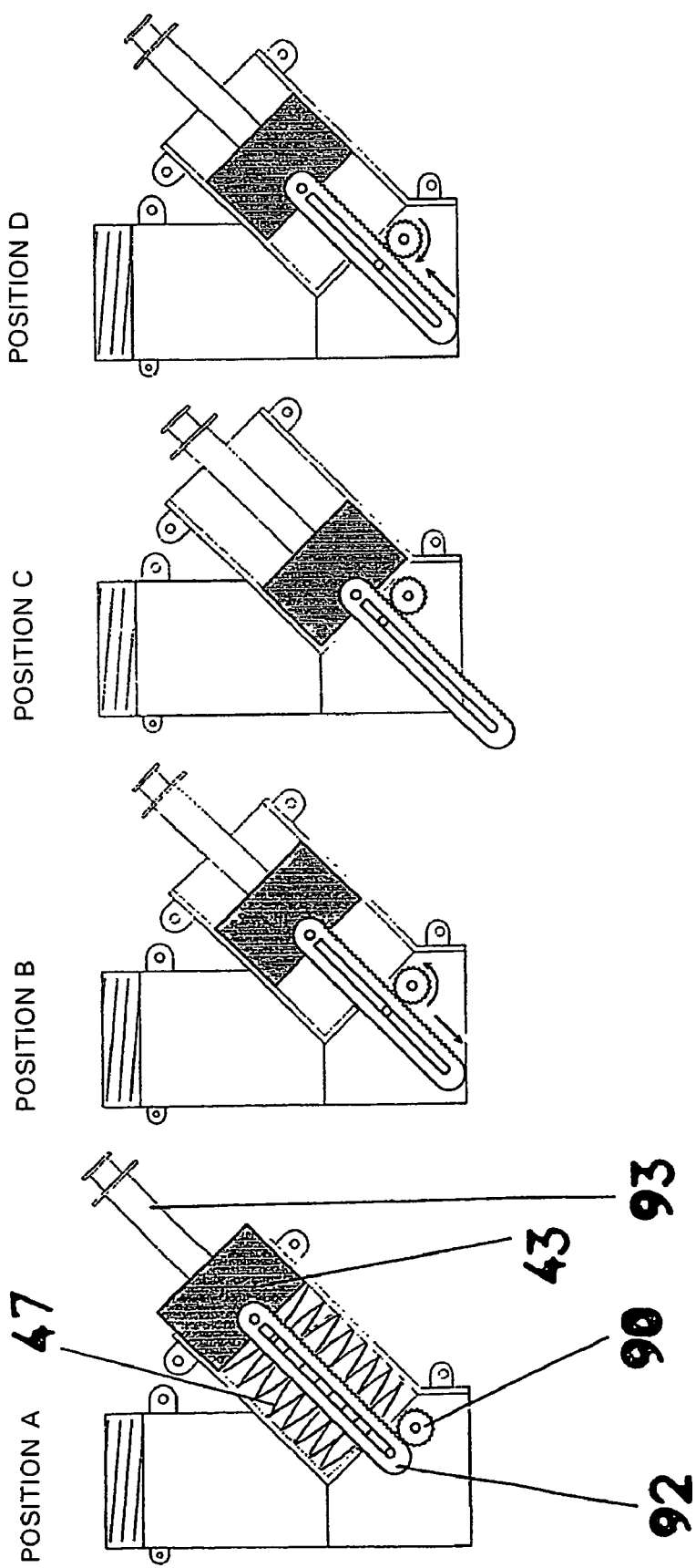
FIG. 13. shows the different positions carried out by the cylindrical part in its path which, when going up or down, makes the gear wheel move by means of an also geared part and this gear wheel in turn makes the solid contacts move without any type of motor.

The disposal of the sharp cutting objects, generally referenced with 40, is carried out as indicated in FIG. 13, the cylindrical part 43 pressed by the syringe 93, the latter moves downwards and in its movement, makes the toothed part 92 slide, causing the rotation of the gear wheel 90 and pressing on the spring 47, thus, as can be seen in FIGS. 11 and 12, there being a gear wheel 90' in the lower part of the tube 20 which in turn actuates the small gear wheels 23 and 24 which, by means of shafts 25 and 25', provide movement to the solid contacts 26 and 27, which are provided with current by means of brushes 28 and 29.

Figure 9:
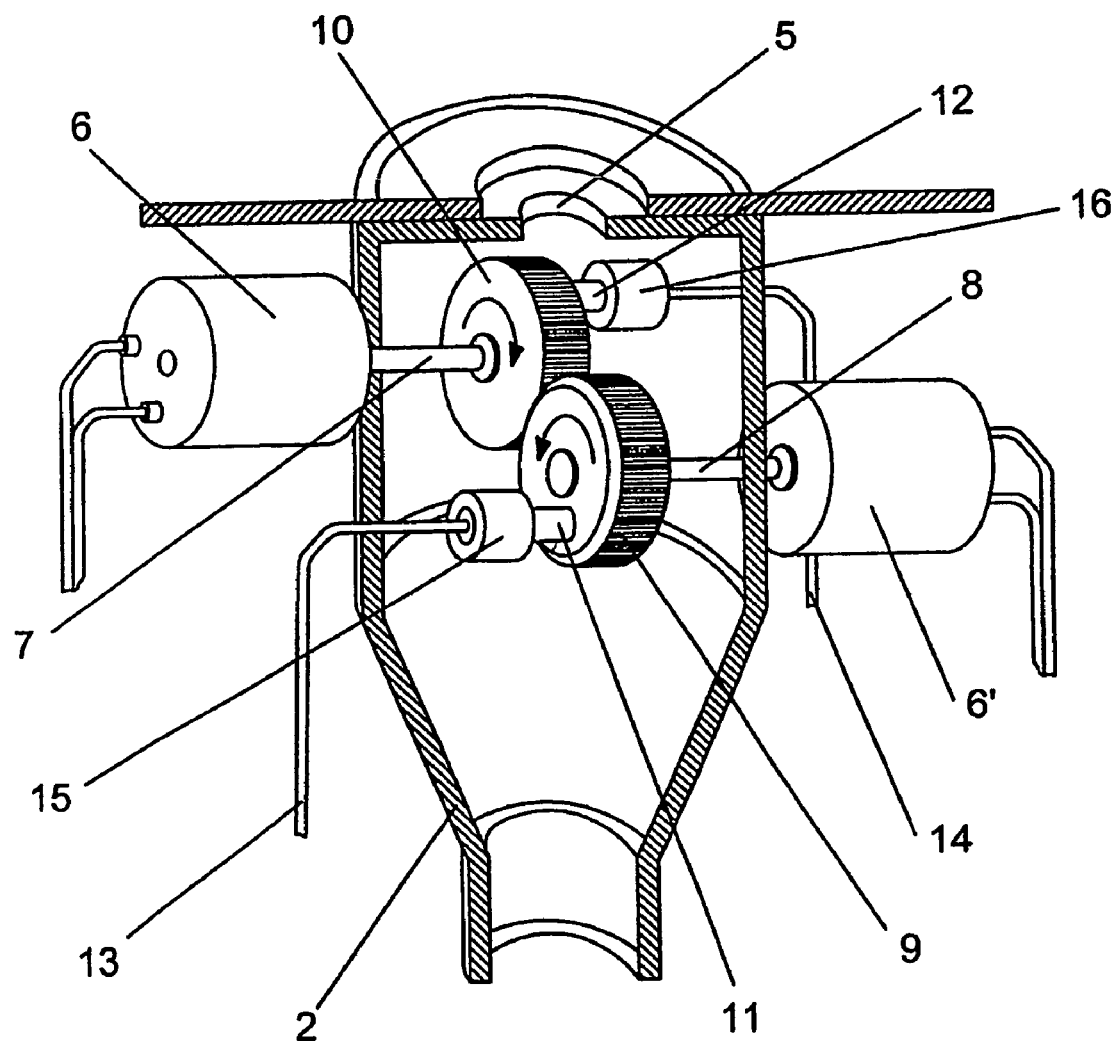
FIG. 9. shows an exploded view of the inside of the tube, showing the two motors and their actuation of the solid contacts.
Figure 10:
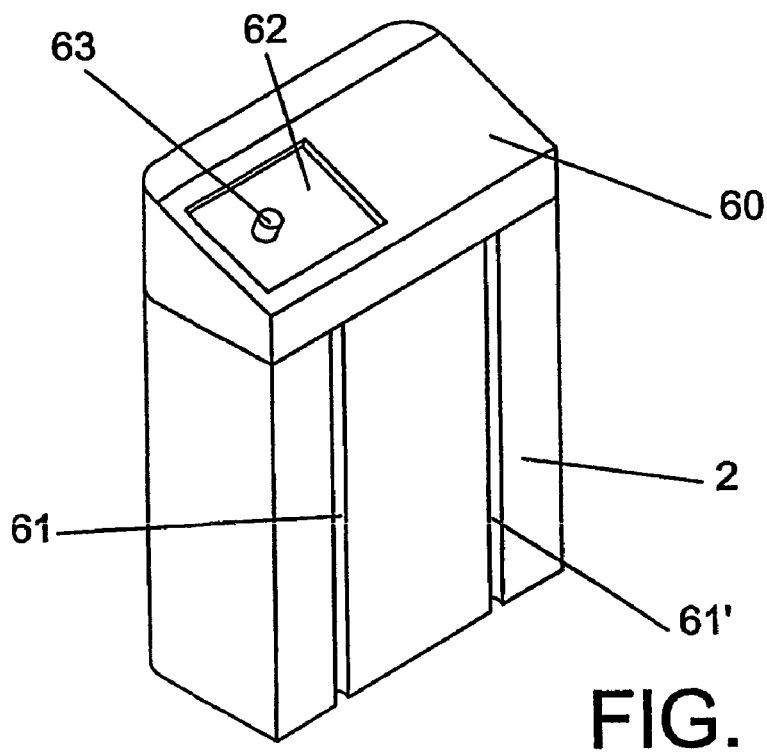
FIG. 10. shows a perspective view of the deposit containing the needleless syringes, where it is possible to see the door with handgrip for accessing the inside.

In a second embodiment, the disposal of the objects 40 can be done as shown in FIG. 9, by means of only one or two motors, motors 6 and 6' being responsible for making the solid contacts 9 and 10 move, which are provided with current by means of brushes 11 and 12 and in turn by means of wires 13 and 14.

The invention is provided with a tube or chimney 30 on the inside thereof, located in the upper part of the solid contacts 26 and 27 incorporated inside the container 2, the tube 30 being intended for facilitating the exhaust of gases produced by melting the sharp cutting objects 40, the gases being retained in the upper part of the tube due to the incorporation of an activated carbon filter 4 which prevents harmful particles from passing through, particles which, due to the effect of the heat produced by melting, will go up this tube 30 where a hollow screw-on cover 32 is incorporated on its upper end for fixing the filter to the tube 30.

Figure 2:
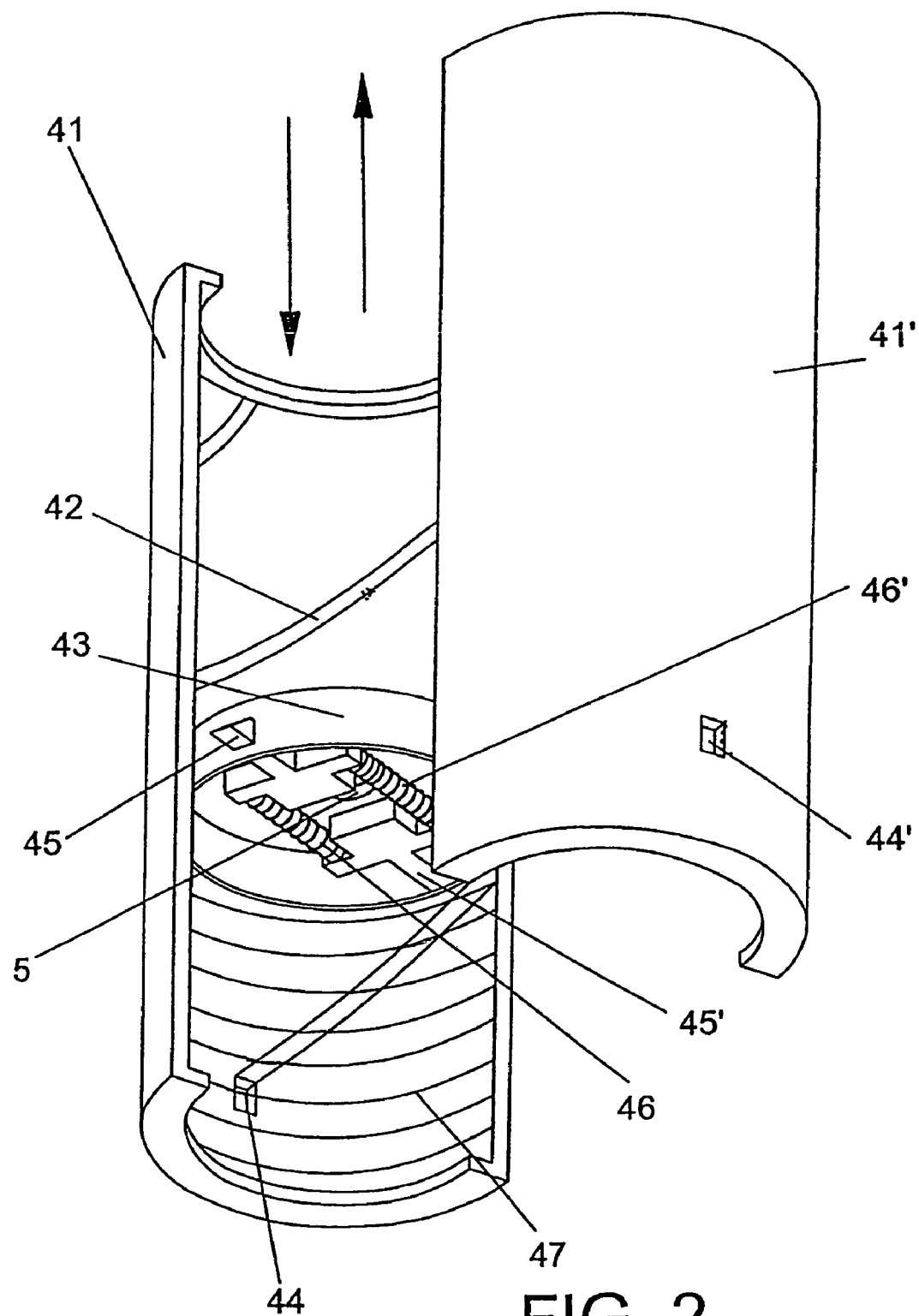
FIG. 2. shows a sectional view of the inner area of the tubular body with the cylindrical part inside it and the so-called "Y" parts in working position.
Figure 8:
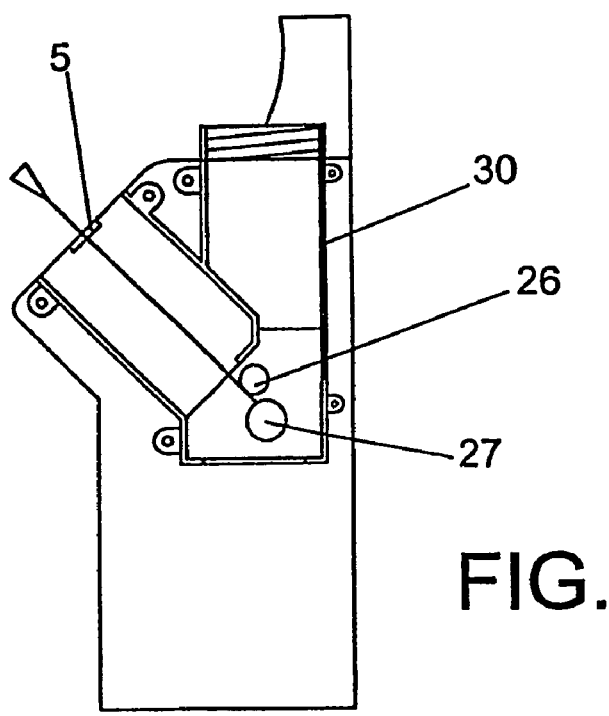
FIG. 8. shows a duly sectioned side elevational view of the object shows in FIG. 7, without showing the syringe container.

It should be indicated that there is another tube at a 45° angle to the vertical of the tube 30 shown in FIG. 8, which, for the purpose of describing it and understanding its inner functioning, has been shown with greater clarity in FIG. 2.

Continuing with FIG. 2, it can be seen that the tube in question is formed by two complementary parts 41 and 41' being intended for serving as a conduit of the needles to the solid contacts where they are disposed of, having means for unscrewing the needles from the so-called "screw on" syringes, since the needles are not coupled to or introduced in these syringes by pressure on the neck thereof, but rather they require being screwed on.

The tube formed by parts 41 and 41' is provided with a helical shaped track or rail 42 inside, the track starting and finishing on both inner sides of the parts and on the inside of the tube thus formed a cylindrical part 43 is provided, whose movement is vertical and rotational inside the bodies 41 and 41' constituting the tube, and at the same time rotational due to the effect created by the track or rail 42, being necessary to indicate that on the inside of the cylindrical part 43 there are two "Y"-shaped metallic parts 45 and 45' which slide horizontally inside of part 43 due to the action of two springs 46 and 46', respectively, which prevent the parts 45 and 45' from joining unless they are kept pressed by their ends or lugs, as shown below.

Figure 3:
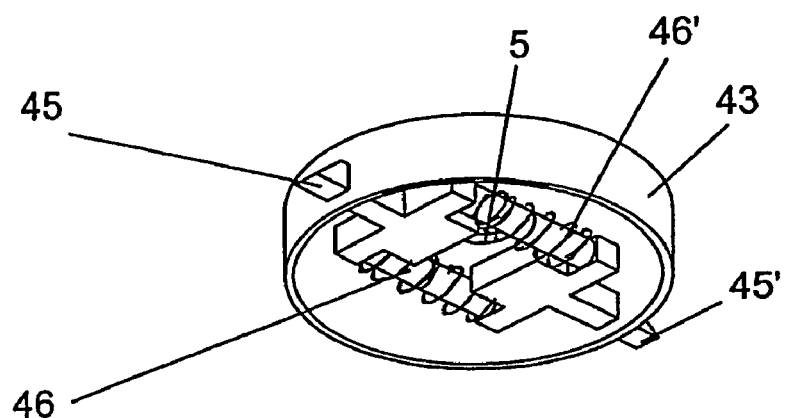
FIG. 3. shows a perspective view of the cylindrical part carrying the springs in working position or closed.
Figure 4:
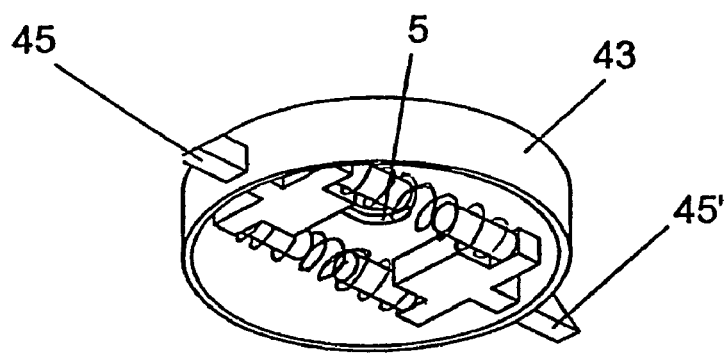
FIG. 4. shows a view similar to the one shown in FIG. 3, the so-called "Y" metallic parts being in standstill or open.
Figure 5:
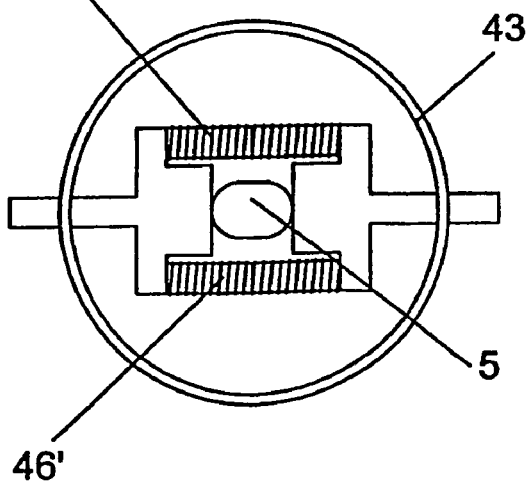
FIG. 5. shows a plan view of the object shown in FIGS. 3 and 4.
Figure 6:
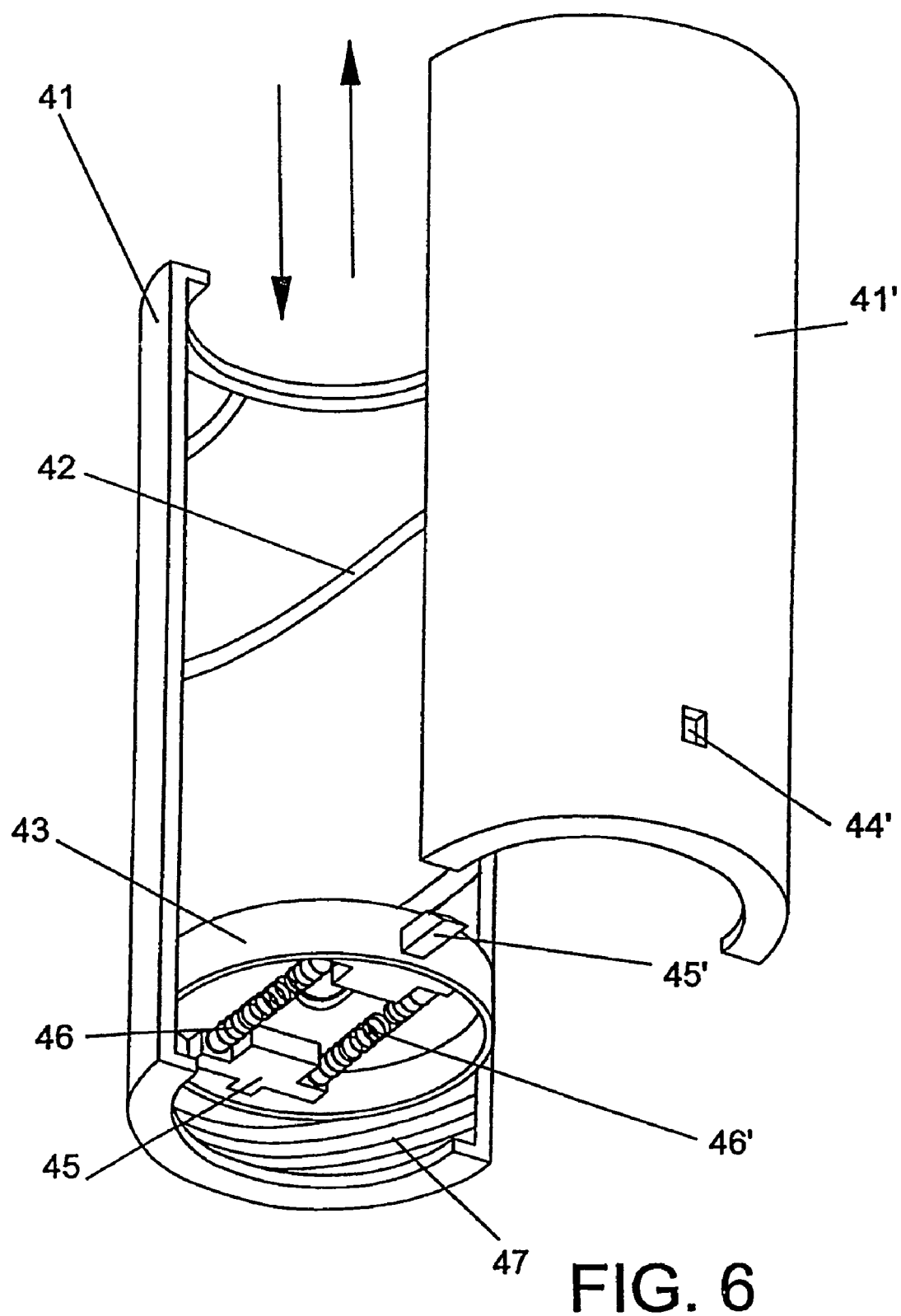
FIG. 6.—again shows a view of the object shown in FIG. 2, but this time the "Y" parts are in standstill state.

As the cylindrical part 43 goes down through parts 41 and 41' due to the pressure of a syringe 93, the cylindrical part will be rotating in a counter-clockwise direction as it goes down from the highest part to the lowest part, pressing on a spring 47 in its path, and during this path, the cylindrical part 43 in a vertical downward direction makes the parts adopting a "Y" shape, referenced with 45 and 45', respectively, stay together at their ends opposite the lugs, as seen in FIG. 3, and upon reaching the lower part of the tube, as seen in FIG. 4 or 6, the lugs will project outwards through the openings 44 and 44', respectively, as a result of the action of the springs 46 and 46'.

Once the pressure created by the syringe against the cylindrical part 43 has stopped and the needle 40 has been unscrewed from the syringe, the upward force of the spring 47 will make the cylindrical part go up again to its upper or standstill position, as it was prior to beginning the actuation thereof.

It must be indicated that in this entire cylindrical part's 43 downward movement process unscrewing the needle 40, the needle has also been disposed of due to the existence of the rotating solid contacts located in the lower part of the tube.

The disposal of a needle 40 and the automatic unscrewing thereof occurs as the needle penetrates the perforation or hole 5, as shown in FIG. 8, and since the lugs of parts 45 and 45' are located inside the tube formed by parts 41 and 41' on their rails 42 pressed against the inner wall of said tube, part 43 will begin to rotate in a counterclockwise direction as it is being pressed by the syringe in a downward direction, unscrewing and disposing of the needle 40 as it approaches the solid contacts 25 and 26, and during this downward movement process of the part 43, the needle is pressed or held by parts 45 and 45'.

Once the cylindrical part has gone down until the end of its path, as shows in FIG. 6, the lugs of parts 45 and 45' will project outwards through the perforations or holes 44 and 44' due to the action of the springs 46 and 46'.

Thus, once the needle cone has been disposed of by the contacts 26 and 27 and unscrewed from the lower end of the syringe, it is free to be incorporated in a container 70 which can be of any nature, as previously mentioned, the container 70 being incorporated in the recipient area 2, which has a cover 60 provided with an access trapdoor 62 and a handgrip 63, likewise provided with several guides 61 and 61' for the fixing thereof to the rear part of the device, as shown in FIG. 7 or 11.

At the same time the syringe stops pressing on the part 43, the latter goes up again due to the force created by the spring 47 which, rotating in a clockwise direction, reaches its standstill position in the upper part of the tube formed by parts 41 and 41'.

The drawer 3 has a disposable container inside of it, made of a rigid plastic material, where the pulverized metal remains are introduced.

Figure 1:
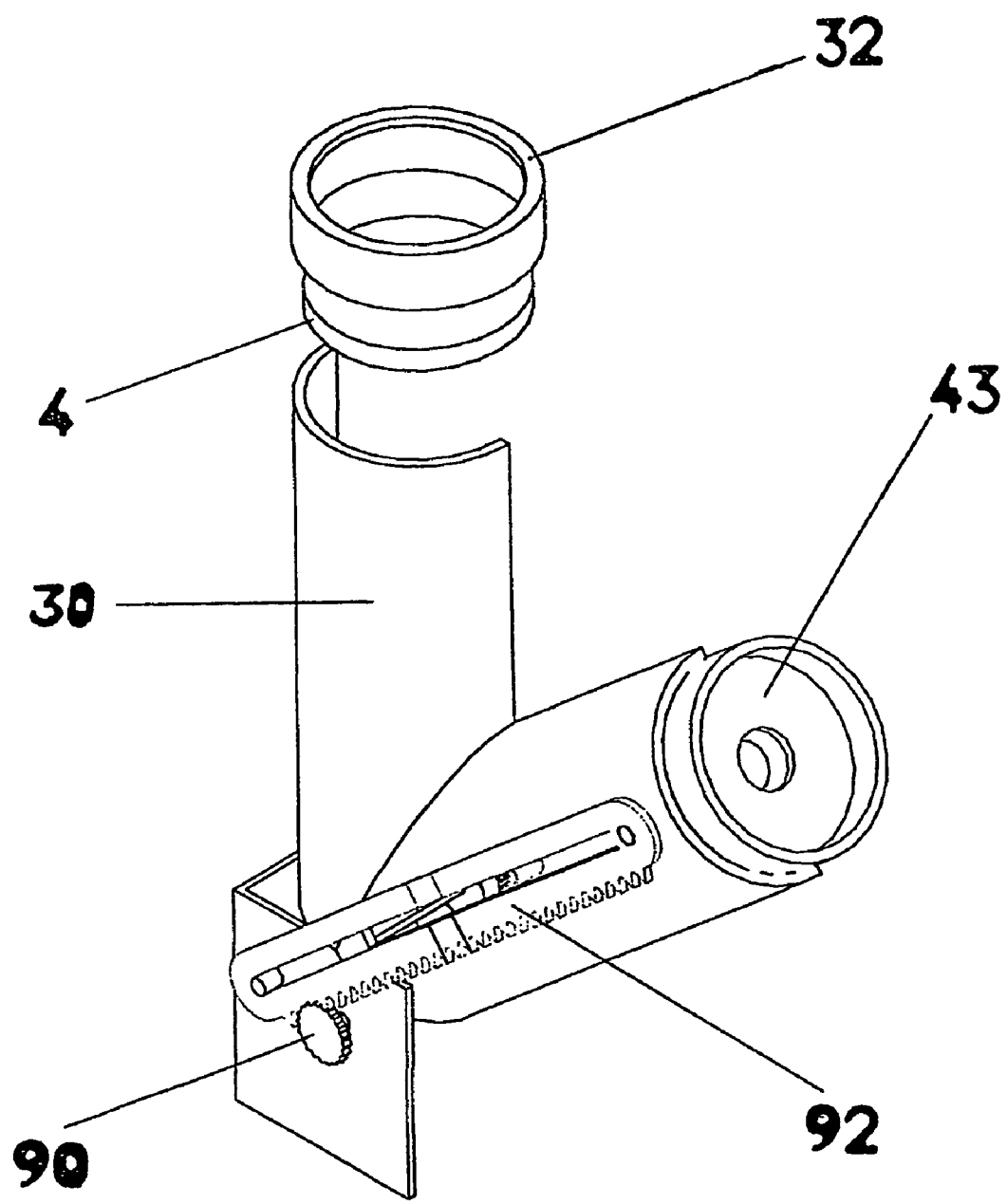
FIG. 1. shows a developed view of the object of the invention regarding a sharp cutting object disposal device provided with means for actuating the gear wheel and with another tube or chute for gas exhaust.

The invention is provided with the pertinent electric transformer or battery 54 which feeds the motors and contacts or, where applicable, only the contacts since the motors are omitted, as shown in FIG. 1.

Figure 14:
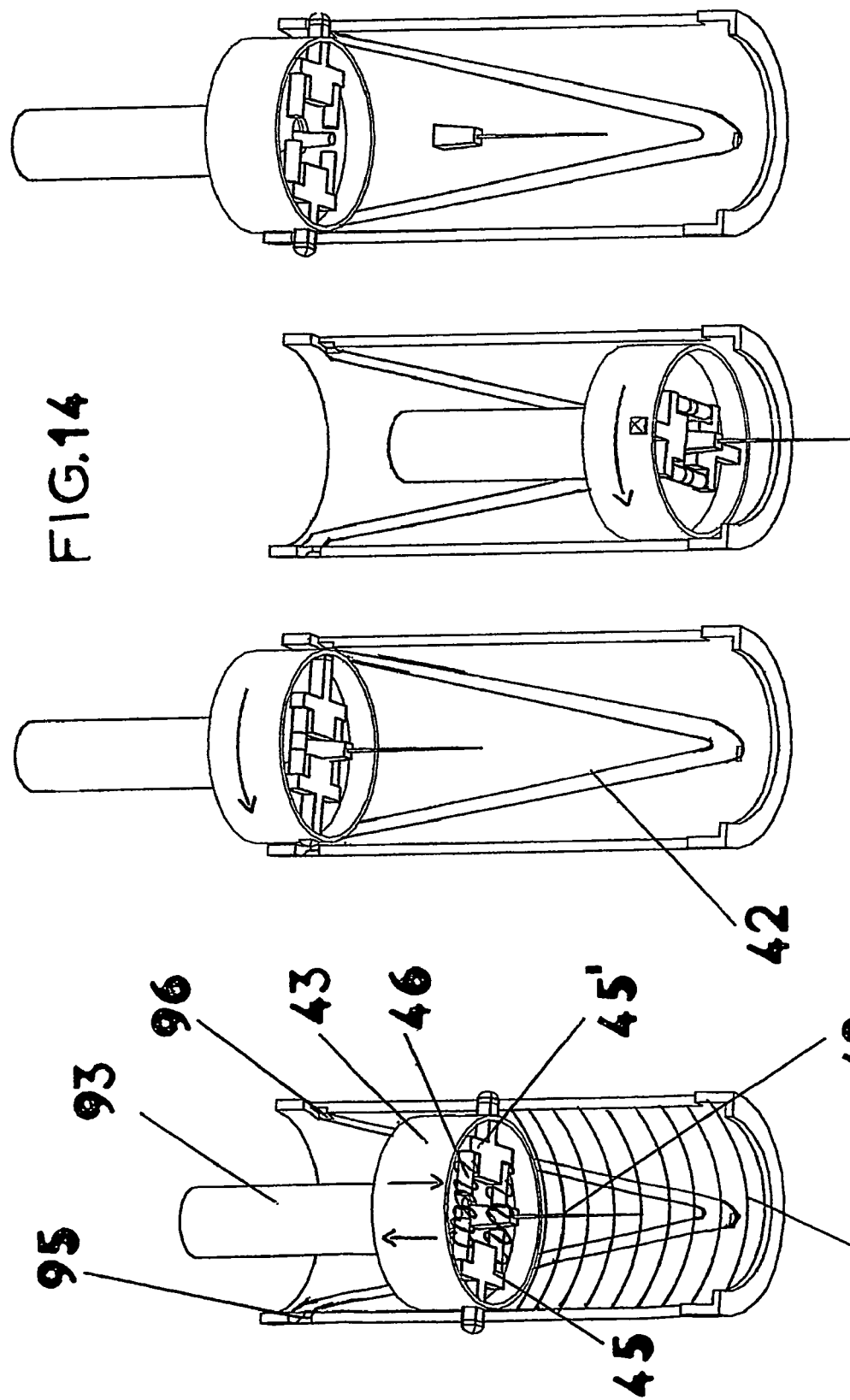
FIG. 14. shows the different positions carried out by the cylindrical part in its path, inside of which movable lugs are housed, and it carries out a 180° rotation in its upward and downward path.

As shown in FIG. 14, another variant of the unscrewing tube can also be placed in which, in this case, the cylindrical part 43 can vertically move up and down in the tube 41 without causing any type of rotation since the parts 45 and 45' have not entered the rail through the ramp 95, or enter through this ramp and go down, rotating in a clockwise direction on the rail 42 and will rotate only 180°, as can be seen in the drawing, in order for the lug 45 to project through the ramp 96, in other words, when the pan 43 is in the lower part of the tube, it will have rotated 90°, and when it goes up again, it will turn another 90°.

Figure 15:
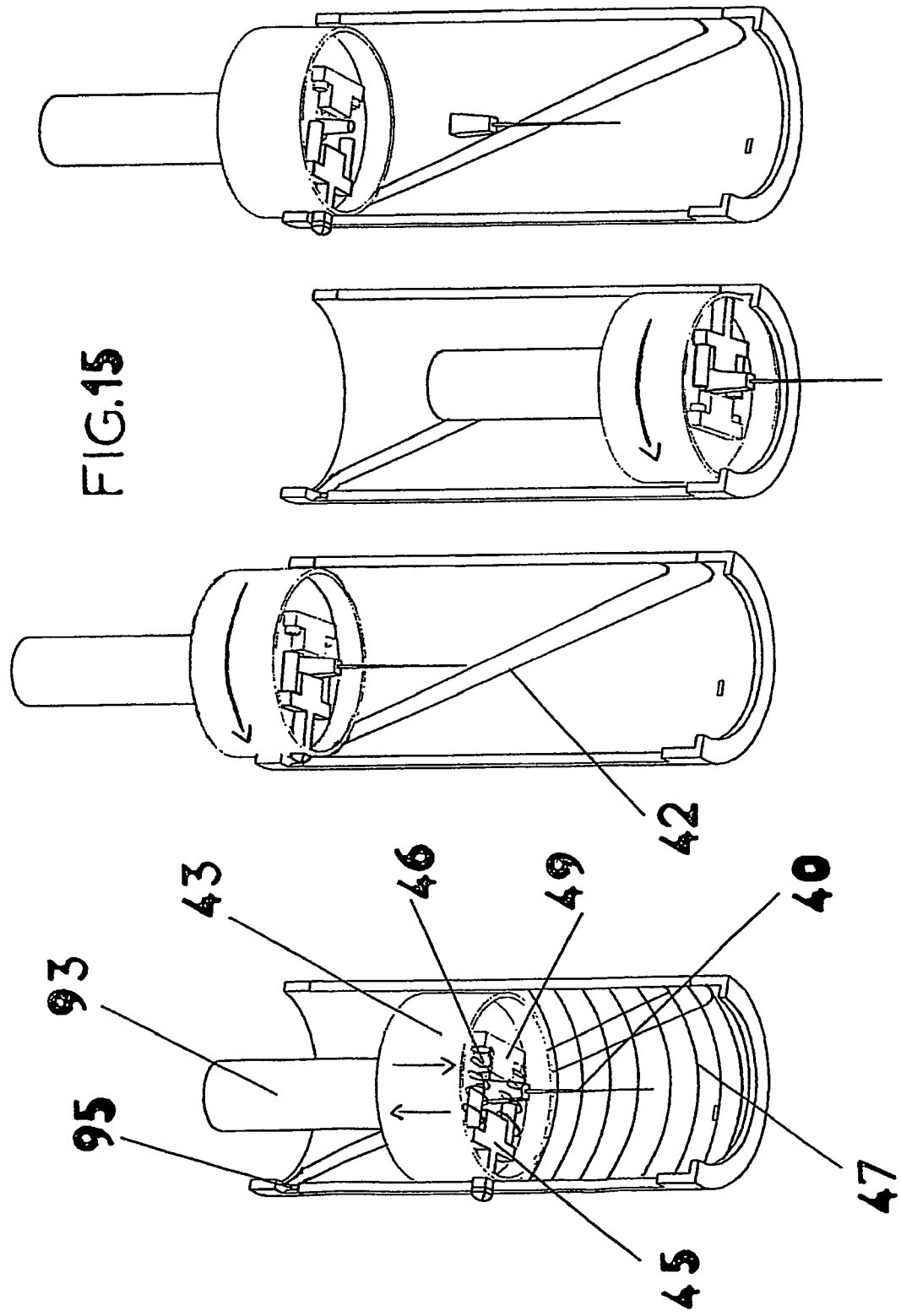
FIG. 15. shows the different positions carried out by the cylindrical part in its path, inside of which a movable lug and another fixed one are housed, and it carries out a 360° turn in its upward and downward path.

There is also the other variant which can be seen in FIG. 15, in which the effect produced by the upward and downward movement of the cylindrical part 43 is the same as in FIG. 14, except that now, there is only a mobile lug 45 and another fixed one 45', as seen in FIG. 16, when the cylindrical part 43 rotates upon entering on the ramp 42 and moves downward, rotating in a clockwise direction on the rail 42, it will now describe a 360° turn, in other words, when the part 43 is in the lower part of the tube, it will have turned 180° and when it goes up again, it will turn another 180°.

Figure 17:
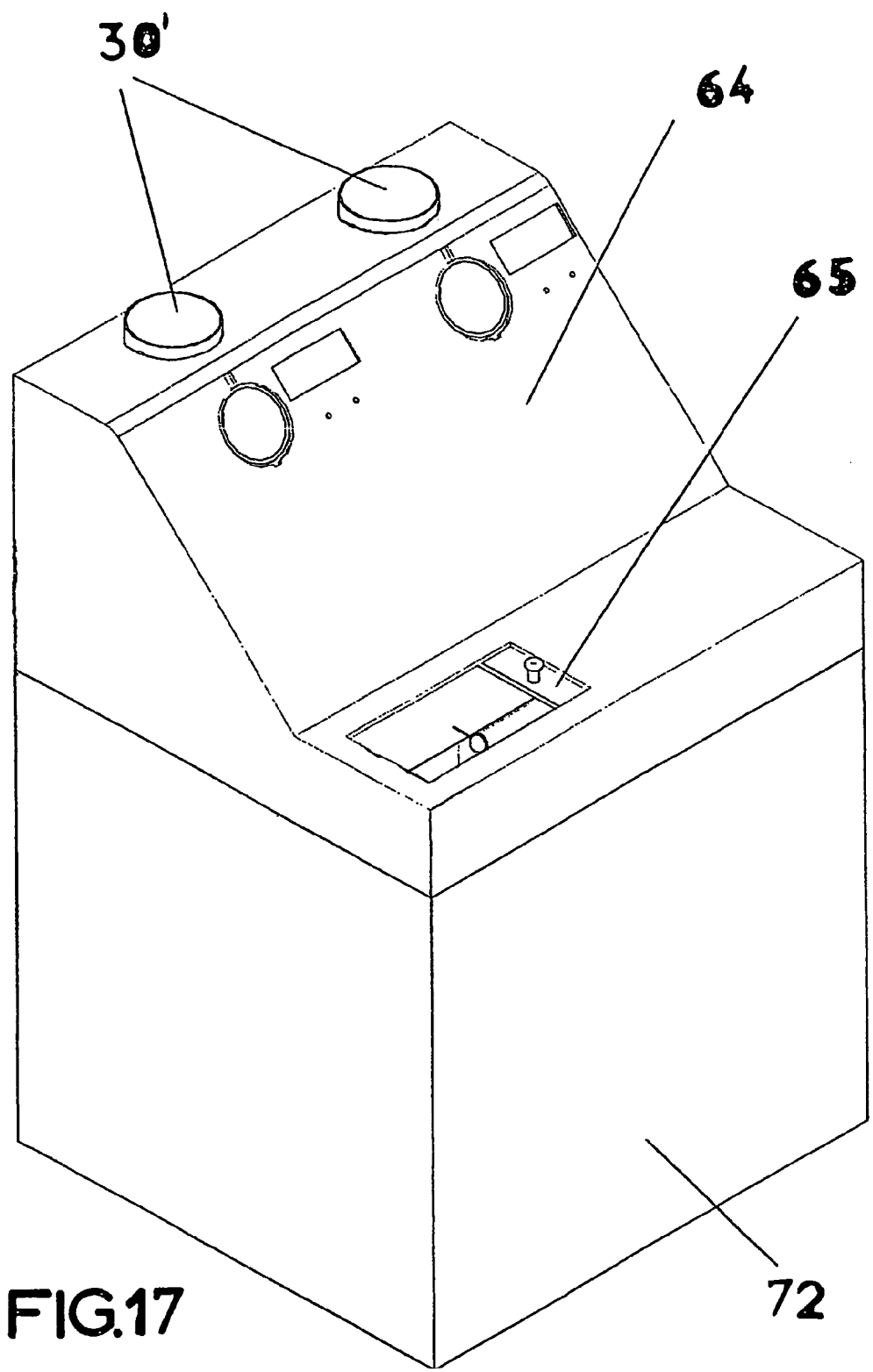
FIG. 17. shows a perspective view of a machine container.
Figure 18:
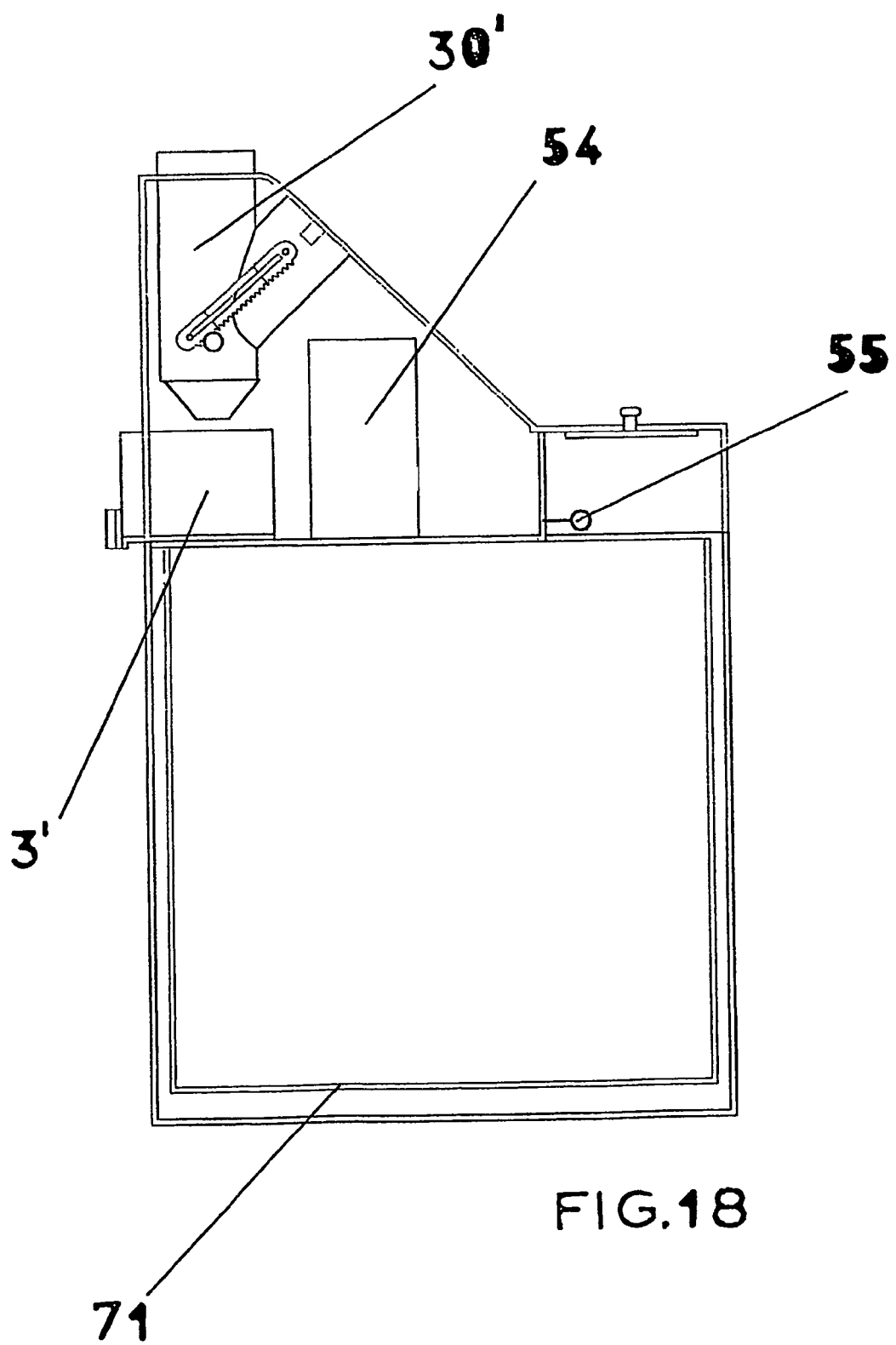
FIG. 18. shows a sectional side view of the machine container, where the tube, drawer, ozone valve and cardboard container for the syringe wastes can be seen on the inside thereof.
Figure 19:
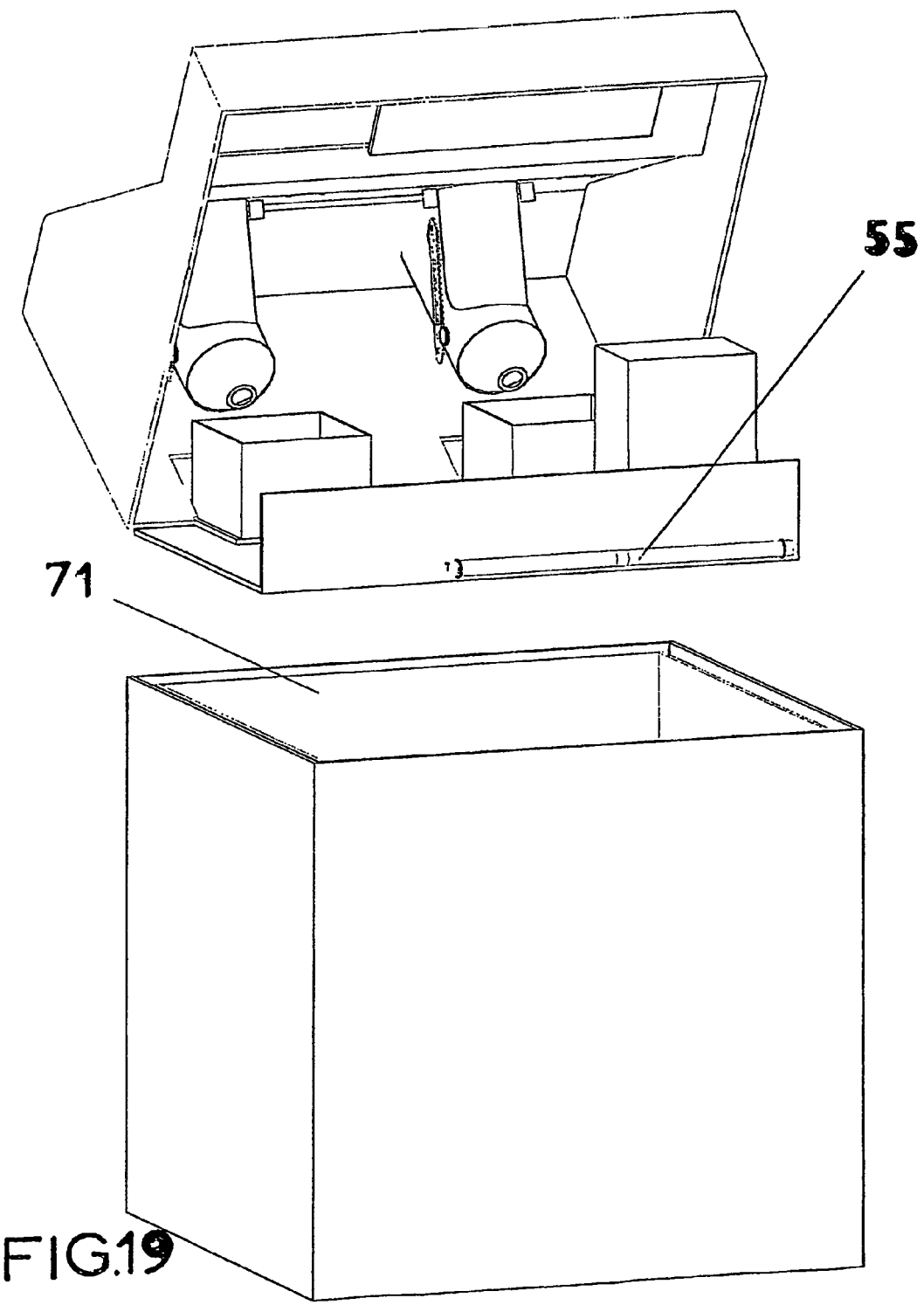
FIG. 19. shows a perspective view of the inside of the machine container, the cover with the machine parts in the upper part separated from the plastic container with its cardboard container on the inside thereof.

Lastly, a drawer-container is disclosed as shown in FIGS. 17, 18, and 19, where all the aforementioned has been introduced, but with the advantage, as seen in these figures, of introducing an ozone or ultraviolet valve 55 in the lower part of the container 72 for sterilizing the syringes placed in the cardboard container 71 once the door 65 has been closed.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. A sharp cutting object disposal device comprising:
    means for unscrewing venopuncture needles from syringes;
    a first container containing said unscrewing means;
    a second container disposed against said first container for storing syringes;
    a drawer disposed within said first container for storing needle waste;
    a gas exhaust system disposed within said first container, said exhaust system including a ventilator, an activated carbon filter on an upper part of said first container, and a hole for receiving sharp cutting objects;
    a pair of shafts rotatably disposed within said first container, each shaft including a contact and a brush;
    a first tube or chimney vertically disposed within said first container, said tube being disposed above said contacts for exhausting gases produced by melting said needle waste;
    a second tube being formed by two complementary tube parts disposed at a 45° angle to said first tube, said second tube directing said needles to said contacts;
    said second tube parts comprising a helical shaped track or rail, said track being entirely disposed on inner sides of said second tube parts;
    a cylindrical part disposed within said second tube, said cylindrical part being axially movable along said track or rail;
    an inside of said cylindrical part including two metallic parts forming a "Y" shape, said metallic parts sliding radially against said cylindrical part, said cylindrical part including two springs for biasing said metallic parts radially outward, said cylindrical part moving axially downward and rotating inside said second tube responsive to biasing from said syringes and communication of said cylindrical part with said track, said needles unscrewing from said syringes responsive to said cylindrical part moving axially downward;
    said second tube having first and second openings disposed at a lower part of said second tube;
    said metallic parts having radially inward and outward ends, said radially inward ends being adjacently disposed and said outward ends defining projecting lugs, each lug being outwardly movable through respective of said first and second openings responsive to biasing from said springs for defining an axially bottommost position of said cylindrical part in said second tube, said needles being unscrewed and separable from said syringes when said cylindrical part is disposed at said axially bottommost position; and
    said second tube further comprising an axially disposed spring, said axial spring biasing said cylindrical part axially upward from said axially bottommost position to a topmost position upon removal of said syringes from said second tube.

2. The sharp cutting object disposal device provided with means for automatic unscrewing of venopuncture needles according to claim 1, characterized in that the second container provided with a cover is internally provided with a cardboard container in which the needleless syringes are incorporated through a trapdoor provided with handgrips.

3. The sharp cutting object disposal device provided with means for automatic unscrewing of venopuncture needles according to claim 2, characterized in that the internally provided container is made of cardboard or is shaped as a plastic bag with a suitable thickness.

4. The sharp cutting object disposal device provided with means for automatic unscrewing of venopuncture needles according to any one of the previous claims, characterized in that there is an ozone or ultraviolet valve inside of the first container which sterilizes wastes dumped in this container.

5. The sharp cutting object disposal device of claim 1, further comprising at least one electric motor and electric conductor disposed within said first container, said motor rotating said shafts.

6. The sharp cutting object disposal device of claim 1, wherein said second tube further comprises an axially disposed geared part and a gear wheel, said geared part connecting with said cylindrical part and said gear wheel communicating with said gear part, said axial geared part being axially movable with said cylindrical part for rotating said gear wheel, said gear wheel communicating with said contacts for rotating said contacts.

* * * * *